US008128227B2

(12) United States Patent
Greenlee et al.

(10) Patent No.: US 8,128,227 B2
(45) Date of Patent: Mar. 6, 2012

(54) METHOD TO DETECT TRANSMISSIBLE SPONGIFORM ENCEPHALOPATHIES VIA ELECTRORETINOGRAM

(75) Inventors: Justin J. Greenlee, Ames, IA (US); Mary Heather West Greenlee, Ames, IA (US)

(73) Assignees: The United States of America as represented by the Secretary of Agriculture, Washington, DC (US); Iowa State University Research Foundation, Inc., Ames, IA (US)

( * ) Notice: Subject to any disclaimer, the term of this patent is extended or adjusted under 35 U.S.C. 154(b) by 402 days.

(21) Appl. No.: 12/423,046

(22) Filed: Apr. 14, 2009

(65) Prior Publication Data

US 2009/0257023 A1   Oct. 15, 2009

Related U.S. Application Data

(60) Provisional application No. 61/045,000, filed on Apr. 15, 2008.

(51) Int. Cl.
*A61B 3/00* (2006.01)

(52) U.S. Cl. ..................................................... 351/200

(58) Field of Classification Search ............... 351/200, 351/205, 246
See application file for complete search history.

(56) References Cited

U.S. PATENT DOCUMENTS

| 4,386,831 A | 6/1983 | Grounauer |
| 4,846,568 A | 7/1989 | Usui |
| 4,874,237 A | 10/1989 | Cringle |
| 5,382,987 A | 1/1995 | Sperling |
| 5,506,633 A | 4/1996 | Sperling |
| 5,539,482 A | 7/1996 | James et al. |
| 6,419,361 B2 | 7/2002 | Cabib et al. |

OTHER PUBLICATIONS

Katz, Bradley J et al, Selective Loss of the Electroretinogram B-wave in a patient with Creutzfeldt-Jakob Disease, Jun. 20, 2000, Journal of Neuroophthalmology, vol. 2, 116-118.*
Chabry, Joelle et al, In vivo and in vitro Neurotoxicity of the Human Prion Protein (PrP) fragment P118-135 Independently of PrP Expression, Jan. 15, 2003, The Journal of Neuroscience 23(2), pp. 462-469.*
Ishikawa et al, Electroretinograms in three cases of Creutzfeldt-Jacob Disease with visual Disturbances, 2009, 53:31-34.*

* cited by examiner

*Primary Examiner* — James Greece
(74) *Attorney, Agent, or Firm* — John Fado; Albert Tsui; Lesley Shaw

(57) ABSTRACT

Disclosed is a method for identifying transmissible spongiform encephalopathy in livestock via an electroretinogram, the method comprises producing a biphasic electroretinogram waveform having an a-wave and b-wave from livestock retina in response to photic stimulus, measuring the amplitude of the b-wave, wherein the amplitude is measured from the trough of the a-wave to the peak of the b-wave, measuring the implicit time of the b-wave, wherein the implicit time is measured from onset of photic stimulus to b-wave peak; and comparing said produced waveform to a comparative waveform of livestock known not to have transmissible spongiform encephalopathy, wherein the produced waveform having a decrease b-wave amplitude and increased b-wave implicit time being indicative of livestock having transmissible spongiform encephalopathy.

6 Claims, 7 Drawing Sheets

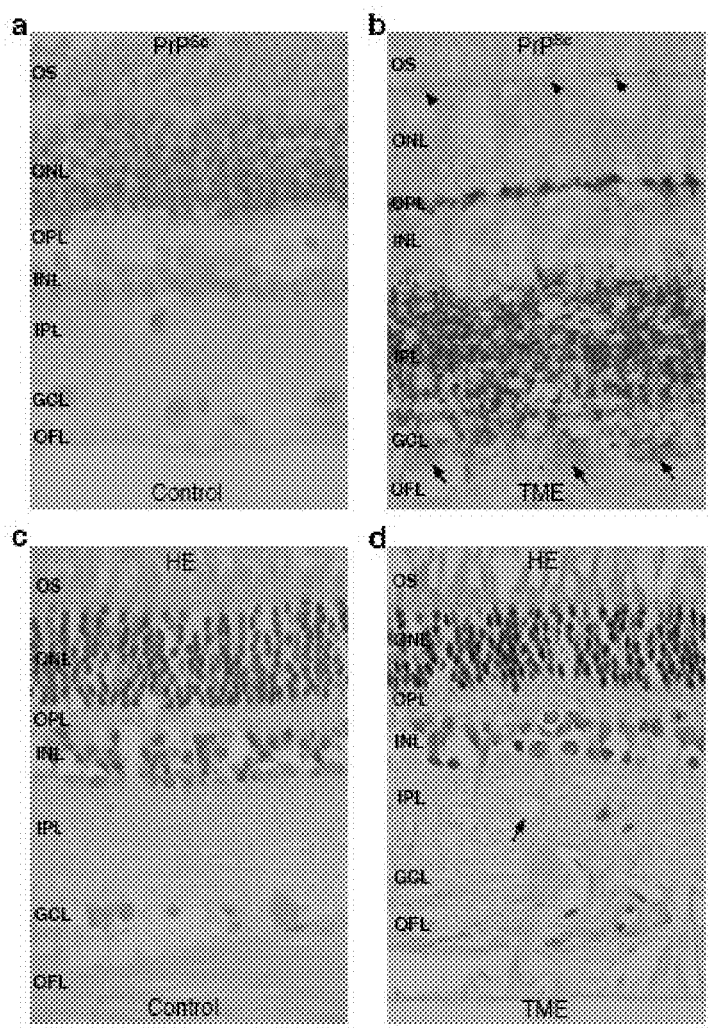
FIGS. 4 A-D

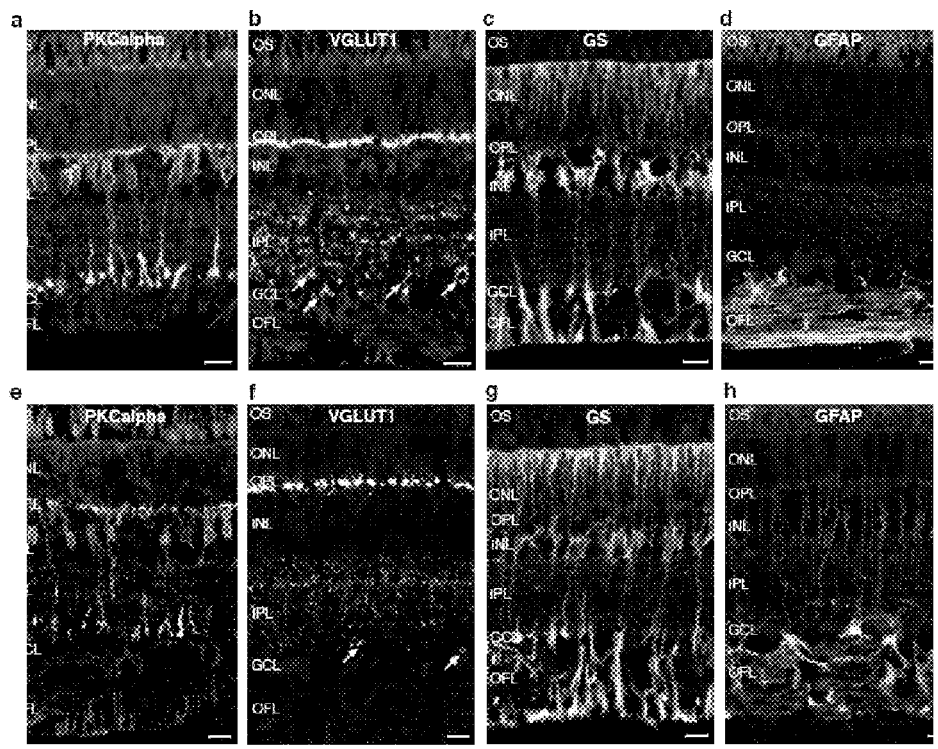
FIGS. 5 A-H

METHOD TO DETECT TRANSMISSIBLE SPONGIFORM ENCEPHALOPATHIES VIA ELECTRORETINOGRAM

CROSS-REFERENCE TO RELATED APPLICATION

This present application claims priority under 35 U.S.C. §19(e) to U.S. Provisional Ser. No. 61/045,000, which was filed on Apr. 15, 2008, the disclosure of which is hereby incorporated by reference.

CONTRACTUAL ORIGIN OF INVENTION

The United States Government has rights to this invention pursuant to Agricultural Research Service, United States Department of Agriculture Specific Cooperative Agreement No.: 58-3625-114 between the U.S. Department of Agriculture and the Iowa State University Research Foundation, Inc.

FIELD OF THE INVENTION

This invention relates to an antemortem method for screening transmissible spongiform encephalopathies or neurodegenerative diseases associated with accumulation of abnormal prion protein in the retina. More specifically, the invention involves measuring electrical potential of a subject retina via measuring said subject corneal response to light stimulation to establish an electroretinogram and analyzing the amplitude of the b-wave and implicit time of the b-wave. Also disclosed is a device for identifying transmissible spongiform encephalopathy in livestock, the device comprising a means for receiving a electroretinogram signal and comparing said signal with the stored data in accordance with at least one program for so comparing and generating an output signal representative of the presence or absence of transmissible spongiform encephalopathy.

BACKGROUND OF INVENTION

Transmissible spongiform encephalopathies ("TSEs") are fatal neurodegenerative diseases presenting as inherited, sporadic, or infectious forms, with the accumulation of an misfolded, protease resistant form of prion protein ($PrP^{Sc}$) in the central nervous system as their pathological underpinning. Examples of disorders in this group include kuru, Creutzfeldt-Jakob disease (CJD), and variant CJD in humans; scrapie in sheep and goats; bovine spongiform encephalopathy in cattle; transmissible mink encephalopathy in mink; and chronic wasting disease in cervids.

The pathobiology, specifically the transmission of and mechanism for infection of transmissible spongiform encephalopathies is not well understood. One hypothesis presumes that a protein confirmation change converts the normal cellular form of the prion protein ($PrP^{C}$) into disease-associated $PrP^{Sc}$. However, it remains uncertain whether $PrP^{Sc}$ is a TSE infectious agent and sole reliance on $PrP^{Sc}$ may not be a reliable marker for TSE infectivity. (Barron, R., et al., 2007. *J. Biol. Chem.*, 282:35878-35886.) Investigation into the pathobiology of TSEs is further complicated when considering the effects of $PrP^{Sc}$ accumulation in natural versus non-natural host species. For example, scrapie-affected sheep (natural host) with demonstrable retinal $PrP^{Sc}$ accumulation by immunohistochemistry do not appear to have associated major morphological changes in their retinas when corresponding hematoxylin and eosin stained sections are examined (Greenlee et al., 2006), whereas retinas from scrapie-affected hamsters (non-natural host) exhibit extensive photoreceptor degeneration (Buyukmichi, N., et al., 1980. *Proc. Natl. Acad. Sci. USA*, Vol. 77, No. 2, 1169-1171; Hogan, R. N., et al., 1981. *Lab Invest*, 44:34-42.).

There is an increased importance placed on studying TSEs in food-producing livestock including scrapie in sheep and goats, bovine spongiform encephalopathy (BSE) in cattle, and chronic waste disease (CWD) in mule deer and elk. For instance, it has been hypothesized that the novel variant form of Creutzfeldt-Jakob disease transmitted to humans as a result of exposure to a BSE agent. Given the uncertainty of the transmissible agent, there is a need to develop detection methods of detection to identify and quarantine livestock before they exhibit clinical signs to prevent transmission at an early stage. One of the factors compounding identifying infected subjects is that incubation for TSEs is relatively long before a showing of clinical signs. Clinical signs of TSEs are usually neurological symptoms and for BSEs, signs include hyperesthesia, hindlimb ataxia, pelvic swaying, hypermetria, tremors, falling, recumbency, and behavioral changes such as apprehension, nervousness, and occasionally frenzy. Non-specific symptoms include loss of condition (wasting), weight loss, and decreased milk production. The incubation period for BSE can be between 30 months to eight years. Given the long incubation period and the importance of livestock, there is a need to develop an antemortem method to detect infected livestock prior to slaughter. Furthermore, early detection of infected livestock would prevent the costly option of slaughtering whole herds of livestock in an effort to quarantine and eliminate infected livestock.

There are postmortem and antemortem screening methods of detecting TSE in livestock. Postmortem detection includes necropsy of subjects showing clinical TSE signs and performing histological and immunohistochemical assays on brain tissue to confirm $PrP^{Sc}$ presence. For instance, U.S. Pat. No. 6,261,790 discloses using monoclonal antibodies in an immunological assay as an indication of the presence of $PrP^{Sc}$. Given the unknown agent for TSE transmissibility, it is imperative that early antemortem diagnosis of livestock be conducted to avert further livestock contamination and prevent transmission to humans.

Electroretinograms ("ERGs") have historically been utilized to detect retinal abnormalities. An electroretinogram is waveform generated by measuring the variation in the electrical potential of the cornea upon photic (light) stimulation. Generally, direct and ground electrodes are applied on or near the subject cornea to record the electrical potential. By altering the visual stimulus and various spatial distributions, ERGs have been utilized to detect deterioration of ganglion cells. (See: U.S. Pat. Nos. 5,539,482, 5,506,633, and 5,382,987 for examples of flashing or pattern alternating stimulation for detecting symptoms related to early glaucoma detection.) Related to TSEs, it is known that $PrP^{Sc}$ can be detected in the retina of cattle with BSE. (Bradley, R. et al., 1999. *Dev. Biol. Stand.*, 99:35-40). In scrapie-affected sheep retina, $PrP^{Sc}$ accumulation is primarily observed in the inner plexiform layer (IPL), the layer of the retina where synaptic connections occur between retinal bipolar, amacrine, and ganglion cells, and the outer plexiform layer (OPL), where synaptic connections occur between horizontal, bipolar, and photoreceptor cells. In both natural and non-natural host species with TSEs, the retina has been shown to accumulate $PrP^{Sc}$ (Bradley, 1999; Foster et al., 1999; Spraker et al., 2002b; Valdez et al., 2003; Head et al., 2003, 2005; Hamir et al., 2004, 2005; Kercher et al., 2004; Hortells et al., 2006; Greenlee et al., 2006). ERGs have been utilized to report a correlation of electroretinographic and histopathologic findings in the eyes of mice infected with scrapie. (Curtis, et al., 1989. *Neuropathology and Applied Neurobiology*, 15: 75-89.) For humans having clinical signs of Creutzfeldt-Jakob disease, it has been reported that 250 lux flash under both photopic and scotopic conditions led to a decrease in B1-wave and abnormal B/A ratio (J. de Seze, et al., 1998. *Neurology*, 51:962-967.) No other disclosures of utilizing ERG to detect transmissible spongiform encephalopathies, particularly in livestock, have been reported. As such, there is a need in the field to utilize an electroretinograms system to livestock screen for transmissible spongiform encephalopathies.

BRIEF SUMMARY OF THE INVENTION

Disclosed is a method for identifying transmissible spongiform encephalopathy in livestock via an electroretinogram, the method comprises producing a biphasic electroretinogram waveform having an a-wave and b-wave from livestock retina in response to photic stimulus, measuring the amplitude of the b-wave, wherein the amplitude is measured from the trough of the a-wave to the peak of the b-wave, measuring the implicit time of the b-wave, wherein the implicit time is measured from onset of photic stimulus to b-wave peak; and comparing said produced waveform to a comparative waveform of livestock known not to have transmissible spongiform encephalopathy, wherein the produced waveform having a decrease b-wave amplitude and increased b-wave implicit time being indicative of livestock having transmissible spongiform encephalopathy. An object of the invention is the method screens livestock that do not exhibit any clinical signs of transmissible spongiform encephalopathy and determine whether the subject is a preclinically or subclinically infected with $PrP^{Sc}$. An advantage of the method is the electrophysiological test can be performed under scotopic or photopic conditions on the livestock. Another advantage is that the invention can be utilized to determine whether genus *Ovis* or genus *Bos* livestock are infected with transmissible spongiform encephalopathy in an antemortem manner.

Another advantage of the invention is that the antemortem method identifies physical change of infected livestock upon photic stimulation. Specifically, infected livestock electroretinogram depict b-wave implicit time between approximately 23 to approximately 33 percent greater than the b-wave implicit time of uninfected livestock in scotopic conditions. Under photopic conditions, livestock depict an approximately 18 to approximately 23 percent greater for same in photopic conditions. Similarly, infected livestock electroretinogram depict b-wave amplitude between approximately 22 to approximately 24 percent lower than the b-wave amplitude of uninfected livestock in scotopic conditions. Under photopic conditions, livestock depict an approximately 20 to approximately 31 percent lower for same in photopic conditions.

Utilizing the disclose electroretinogram method, livestock of the genus *Ovis* produced b-wave implicit time approximately 86 percent greater than the b-wave implicit time of the comparative waveform under scotopic conditions. Also, the produced livestock of the genus *Ovis* produced b-wave amplitude between approximately 39 percent to approximately 54 percent lower than the b-wave amplitude of the comparative waveform under scotopic conditions. The method disclosed a comparative waveform that is an electroretinogram of livestock of the genus *Ovis* known not to be infected with transmissible spongiform encephalopathy.

In another embodiment, disclosed is a method for screening Bovine having no clinical signs of transmissible spongiform encephalopathy via an electroretinogram, the method comprising producing a electroretinogram waveform having b-wave from Bovine retina in response to photic stimulus, measuring the implicit time of the b-wave, wherein the implicit time is measured from onset of photic stimulus to b-wave peak; and comparing said produced waveform to a comparative waveform of Bovine known not to have transmissible spongiform encephalopathy, wherein the produced waveform having an increased b-wave implicit time being indicative of Bovine having transmissible spongiform encephalopathy.

Also disclosed is a device for identifying transmissible spongiform encephalopathy in livestock, the device comprising a means for receiving a electroretinogram signal measuring the electrical response of livestock retina in response to photic stimulus, said signal characterized by having a b-waveform; a programmable memory unit having stored electroretinogram waveform data, said data having b-waveform of livestock known not to have transmissible spongiform encephalopathy; a means for processing the received electroretinogram signal and comparing said signal with the stored data in accordance with at least one program for so comparing and generating an output signal representative of the presence or absence of transmissible spongiform encephalopathy; and an output means responsive to said output signal registering an indication of the presence or absence of transmissible spongiform encephalopathy.

BRIEF DESCRIPTION OF THE DRAWING

The present invention together with the above and other objects and advantages may best be understood from the following detailed description of the embodiment of the invention illustrated in the drawings, wherein:

FIGS. 4A-D depict photomicrographs of retinal tissue from control and TSE infected cattle indicating PrPSc-immunoreactivity throughout both plexiform layers, within retinal ganglion cells (arrow), and sporadically within the inner nuclear layer and at the outer limiting membrane (arrowheads) in retinas from TME-affected cattle as indicated in FIG. 4B.

Figure 1:
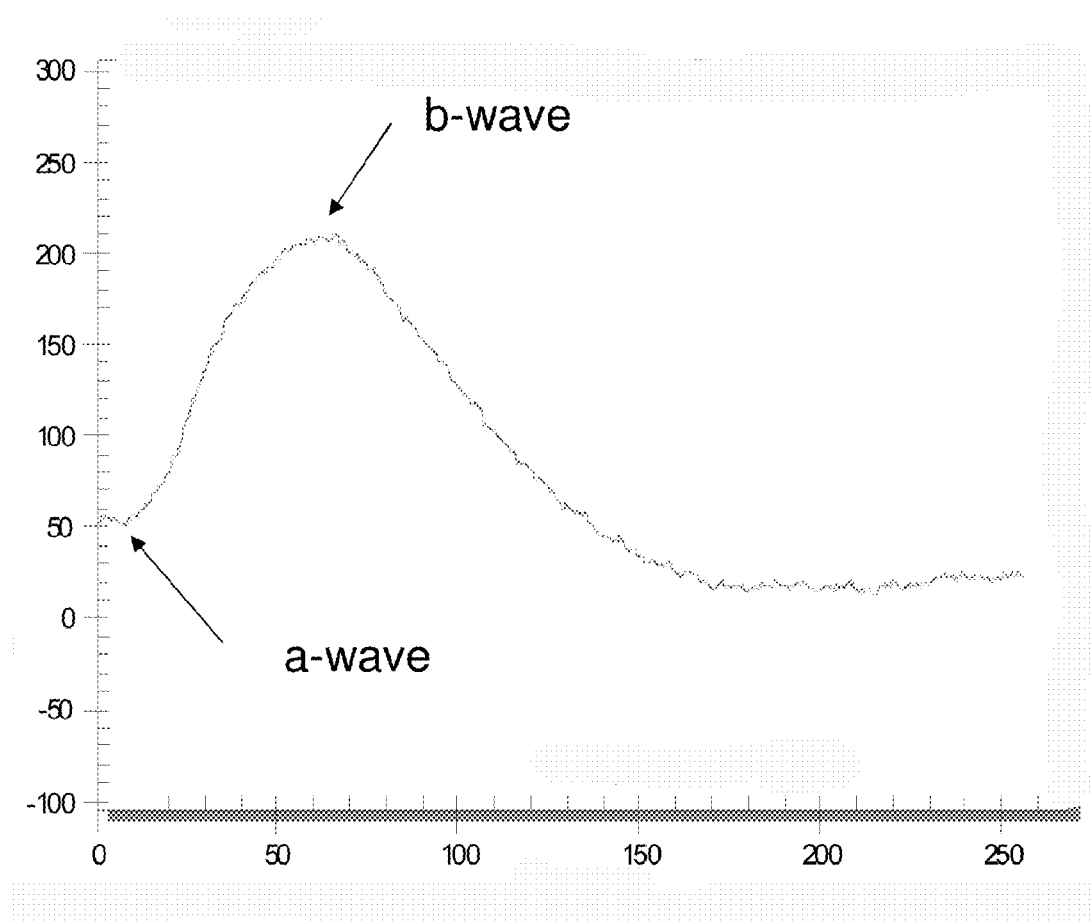
FIG. 1 is a graphic depicting an electroretinogram with electric potential difference ($\mu V$) as a function of time (msec) with a biphasic a-wave and b-wave as indicated.
Figure 2A:
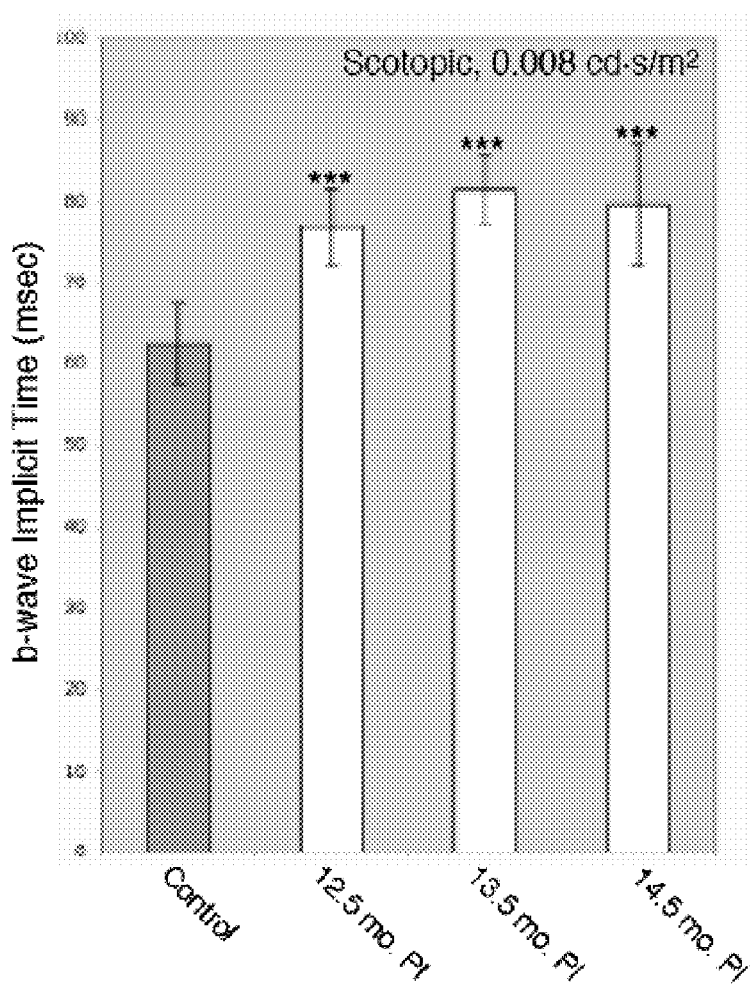
FIGS. 2A, B, and C are graphs of b-wave implicit time of Holstein cattle either in non-inoculated, preclinical, or clinical stage of transmissible spongiform encephalopathy.
Figure 2B:
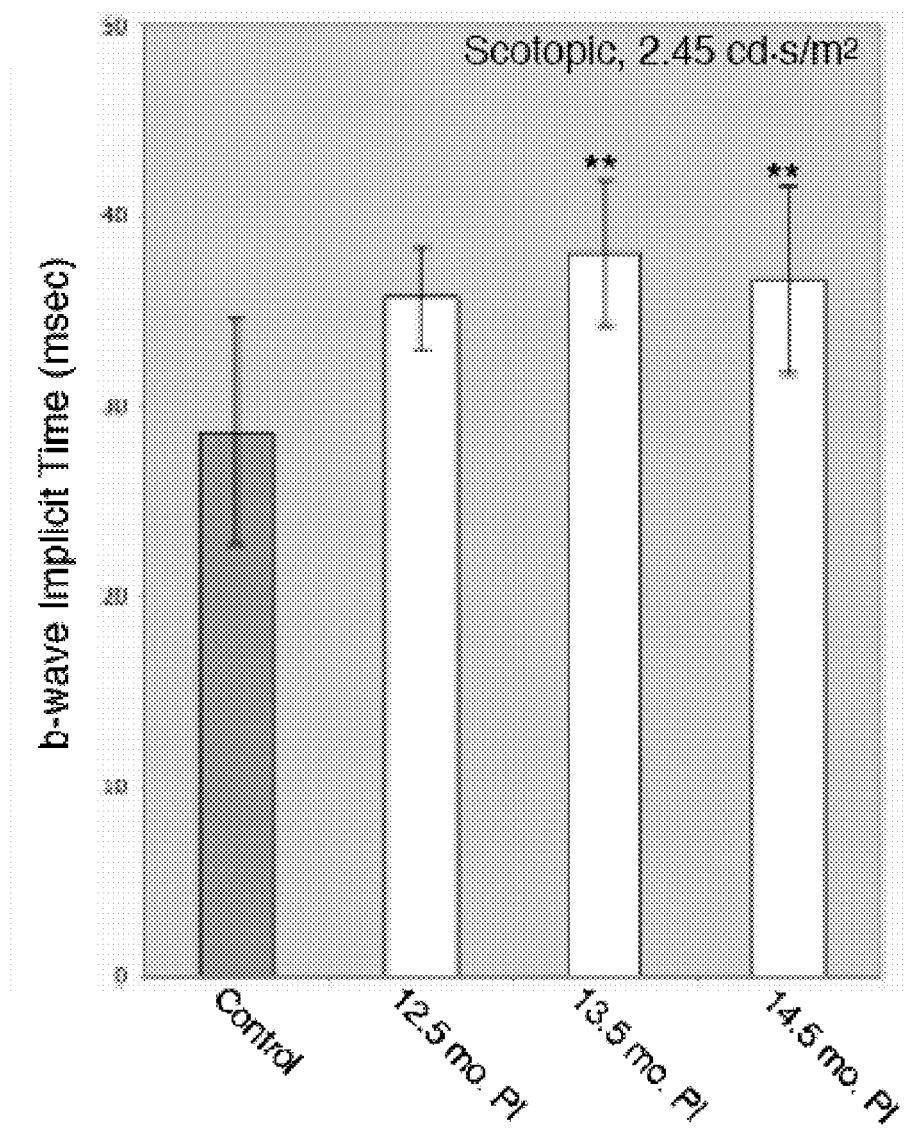
Figure 2C:
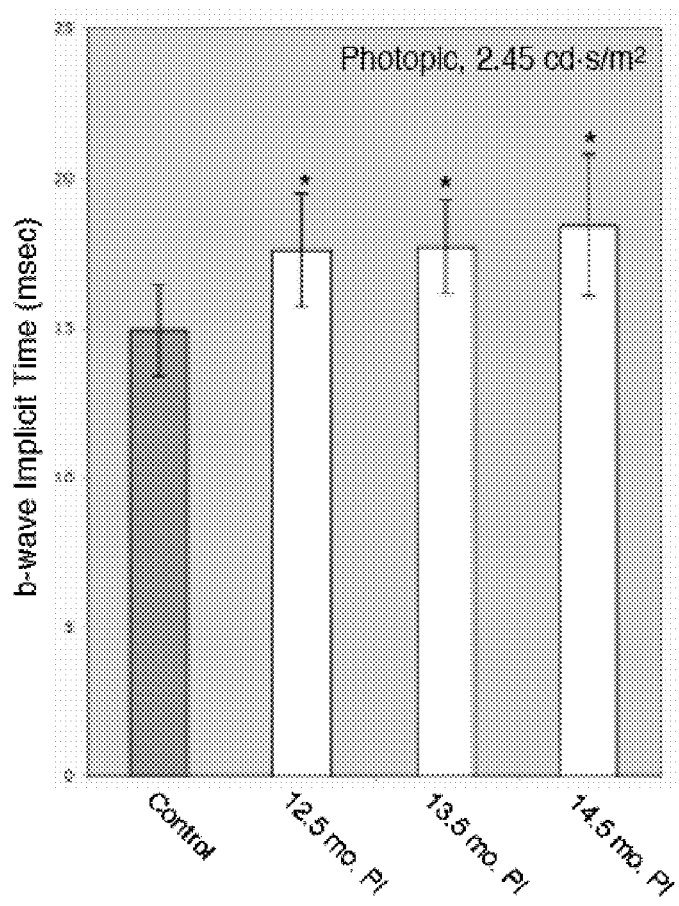

Retinal sections from control and TME-affected cattle were stained with hematoxylin and eosin as indicated in FIGS. 4C and D revealing multifocal vacuoles within the IPL (arrows) and decreased numbers of nuclei in the GCL. For FIGS. 4A-H and FIGS. 5A-H, the photomicrographs indicated abbreviations of: OS, outer segments; ONL, outer nuclear layer; OPL, outer plexiform layer; INL, inner nuclear layer; IPL, inner plexiform layer; and GCL, ganglion cell layer.

FIGS. 5A-H depict photos of immunohistochemical stains of retina tissue of TSE infected cattle. Immunoreactivity (-IR) patterns of PKCα, VGLUT1, GS, and GFAP in the retinas of control are depicted in FIGS. 5A-D while FIGS. 5E-H depict TME-affected cattle.

DETAILED DESCRIPTION OF THE INVENTION

Definitions

As used in the specification and claims, the singular form "a", "an" and "the" include plural references unless the context clearly dictates otherwise. For example, the term "a waveform" includes a plurality of waveforms or multiple waveform trials.

The term transmissible spongiform encephalopathies refers to a family of neurodegenerative diseases that manifest through an accumulation of abnormal proteinaceous infectious particle (prions) in the brain, central nervous system, or neural tissue of a subject. Examples of diseases caused by prions in animals include scrapie in sheep and goats, bovine spongiform encephalopathy in cattle, transmissible mink encephalopathy in mink, chronic wasting disease in elk and mule deer, feline spongiform encephalopathy in feline, exotic ungulate encephalopathy in nyala, oryx and greater kudu. Examples of disease caused by prions in humans include variants of Creutzfeld-Jakob Disease, Gerstmann-Sträussler-Scheinker syndrome, fatal familial insomnia, sporadic fatal insomnia, and Kuru.

Livestock infected with transmissible spongiform encephalopathies typically show clinical signs of infection. For *Bos* these signs include changes in temperament, such as nervousness or aggression, abnormal posture, incoordination and difficulty in rising, decreased milk production, or loss of body weight despite continued appetite. For *Ovis* progressive decrease in appetite and associated weight loss, fine head tremors, listlessness, progressive problems with locomotion, and terminal sternal recumbency are signs of clinical infection.

As used herein, the term electroretinogram is a waveform produced by light-evoked electrical response of cells in the retina. The waveform produced generally has two readily identified components, namely: a-wave and b-wave. The electroretinogram has an initial negative deflection that is the a-wave, which is followed by a large positive deflection, the b-wave. The b-wave amplitude was measured from the trough of the a-wave to the peak of the b-wave. The b-wave can result in multiple oscillatory potentials, wherein the peak is measure at the highest electric potential difference point. Additionally, a measurement of implicit of the b-wave can be gathered from an electroretinogram. As used herein, the implicit time is time measure from the onset of photic stimulus to the time the b-wave reaches the amplitude peak.

Electroretinography

To evaluate retinal function in TME infected livestock, flash electroretinography can be conducted under both dark- (scotopic) and light- (photopic) adapted testing conditions. Under scotopic conditions, the livestock was allowed to dark-adapt within a light-proof Faraday cage for 20 minutes prior to ERG testing.

Figure 3:
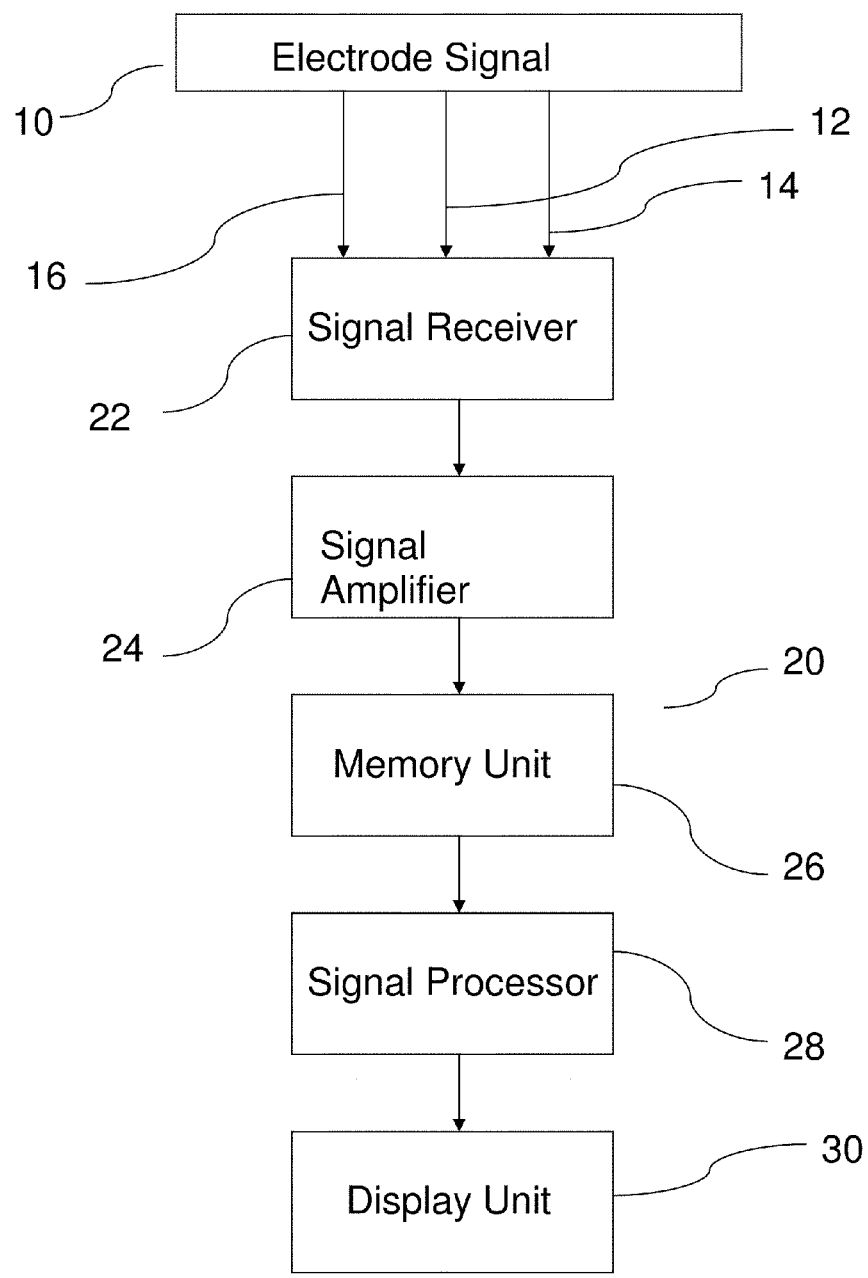
FIG. 3 is a block figure schematic for a handheld device for identifying transmissible spongiform encephalopathy in livestock.

In reference to FIG. 3, the ERG test is optimally conducted via placing a plurality of electrodes is on the test livestock subject to elicit an electrode signal 10 upon photopic response. In one embodiment, an ERG electrode signal 10 is generated form a cornea electrode signal 12, a reference electrode signal 14, and a ground electrode signal 16. The cornea electrode signal is the result of a DTL Plus microfiber electrode (LKC Technologies, Gaithersburg, Md.) positioned on the unanesthetized cornea and adhered to the skin near the medial and lateral canthi of livestock to be tested. Subdermal 12 mm, 29 gauge needle electrodes (LKC Technologies, Gaithersburg, Md.) were used as reference and ground. The reference electrode was placed subcutaneously approximately 2 cm caudal to the lateral canthus, and the ground electrode was placed subcutaneously in the region overlying the occipital bone. Those electrode signals are received by an electrodiagnostic system 20. For instance the cornea, reference, and ground electrodes are connected to an EPIC 4000 visual electrodiagnostic testing system (LKC Technologies, Gaithersburg, Md.). The system utilizes a signal receiver 22 to receive the electrode signals housed in the system. The system utilizes an amplifier bandwidth 24. Optimally, the bandwidth is set at 0.3 to 500 Hz, with the high-pass (low-frequency) filter adjusted from 0.3 to 75 Hz in order to isolate oscillatory potentials. Additionally, the system incorporates a memory unit 26. The memory unit having stored data of ERGS of uninfected TSE livestock. The system also houses a signal processor 28 to compare the ERG signal received with the ERG stored in the memory unit 26. The system is configured to output a signal to a display unit 30. Optimally, the display unit displays whether the ERG electrode signal contain abnormal b-wave amplitude and b-wave implicit time in comparison to the ERG data stored in the memory unit. In one embodiment, a CMGS-1 Color Mini-Ganzfeld Stimulator (LKC Technologies, Gaithersburg, Md.) was used to elicit the ERGs.

The following non-limiting examples are provided to further illustrate various embodiments of the present invention.

EXAMPLE 1

ERG of Transmissible Mink
Encephalopathy-Inoculated Holstein Cattle

Five Holstein steers were inoculated intracerebrally with brain homogenate prepared transmissible mink encephalopathy (TME) at 9-months of age and evaluated prior to clinical signs of disease at 12.5, 13.5, and 14.5 months post-inoculation, and at 18.5 months. All cattle developed clinical disease and were euthanized when deemed humanely necessary at between approximately 16.5 to 19 months post-inoculation. Inoculated steers were housed in a Biosafety Level 2 isolation barn (two animals per pen) at the National Animal Disease Center (NADC), Ames, Iowa. They were fed pelleted growth and maintenance rations that contained no ruminant protein, and clean water was available ad libitum. Control steers were housed together in an open shed and fed the pelleted growth ration (without ruminant protein) and alfalfa hay. Personnel wore protective clothing while in the isolation facility and showered before leaving the facility. Additionally, 10 non-inoculated Holstein steers were housed in the same building as the TME-inoculated cattle and served as control animals for ERG analysis.

For ERG analysis, each steer was allowed to dark-adapt within a light-proof Faraday cage for 20 minutes prior to testing. Animals were lightly sedated with 0.02 mg/kg xylazine prior to auriculopalpebral nerve block and electrode placement. Mydriasis was induced with topical administration of 1% tropicamide ophthalmic solution to the cornea 10 minutes prior to testing. One eye was tested in each animal. Palpebral akinesia was achieved by anesthetizing the auriculopalpebral nerve with 3-5 mL of 2% lidocaine hydrochloride injectable solution infused subcutaneously over the nerve. Throughout the testing period, an aqueous solution was applied to the corneal surface to prevent desiccation, and artificial tear ointment was applied to the examined eye at the end of the testing procedure. Xylazine-induced sedation was reversed with 2 mg/kg tolazoline as necessary. Cattle were dark adapted for 20 minutes, followed by a series of 9 scotopic single white flash recordings ranging in intensity from 0.008 to 24.5 cd·s/m², and 1 photopic response (2.45 cd·s/m²) after 10 minutes of light adaptation.

Inoculum and Inoculation Procedure

The inoculum was procured from a Holstein steer (No. 2) which had been intracerebrally inoculated in 1990 with TME and had developed spongiform encephalopathy. The brain material from the steer was a 10% brain suspension (wt/vol) and had been stored at −70° C. The original source of the TME was from a Stetsonville, Wis., outbreak of TME in mink in 1985. The brain tissue was ground in a mechanical grinder, gentamicin was added at 100 μg/ml, and the final concentration of 10% (wt/vol) was made with phosphate buffered saline.

Steers were inoculated intracerebrally with 1 ml of TME. The steers were sedated with xylazine, a midline incision was made in the skin at the junction of the parietal and frontal bones, and a 1-mm hole was drilled through the calvarium. The inoculum was injected into the midbrain via a 22-gauge 9-cm-long disposable needle while withdrawing the needle from the brain. The skin incision was closed with a single suture. After each group of inoculations, the surgical instruments, including the drill bit, were discarded. Steers designated as controls were not inoculated.

The b-wave amplitude and implicit time was measured for each scotopic ERG recorded at low (0.008 cd·s/m²) and standard (2.45 cd·s/m²) light intensities, for the photopic response. The b-wave amplitude was measured from the peak of the a-wave to the peak of the following positive deflection. Implicit time was reported as the time between stimulus onset and peak of the b-wave. Table 1 details the results of the ERG response and the mean b-wave amplitude and implicit time. The non-inoculated group was compared to the preclinical TME-inoculated group using the Mann-Whitney U test with a 95% confidence interval. P values less than 0.05 were regarded as statistically significant.

TABLE 1

| Test | Test Condition | Experimental Condition | Mean b-wave amplitude (μV) ± SD | Mean b-wave Implicit time (msec) ± SD |
|---|---|---|---|---|
| 1 | Scotopic, −0.008 cd · s/m² | TME - 12.5 mo. PI | 149.2 ± 65.5 | 77.0 ± 4.7*** |
|   |   | TME - 13.5 mo. PI | 159.9 ± 31.6 | 81.2 ± 4.3*** |
|   |   | TME - 14.5 mo. PI | 174.6 ± 48.3 | 79.5 ± 7.4*** |
|   |   | Non-Inoculated | 140.3 ± 51.5 | 62.4 ± 4.9 |
| 2 | Scotopic, 2.45 cd · s/m² | TME - 12.5 mo. PI | 558.1 ± 168.0 | 35.7 ± 5.9 |
|   |   | TME - 13.5 mo. PI | 549.5 ± 160.0 | 38.0 ± 2.7** |
|   |   | TME - 14.5 mo. PI | 552.3 ± 151.4 | 36.6 ± 3.8** |
|   |   | Non-Inoculated | 720.6 ± 227.1 | 28.6 ± 4.9 |
| 3 | Photopic, 2.45 cd · s/m² | TME - 12.5 mo. PI | 121.3 ± 41.8 | 17.6 ± 1.9* |
|   |   | TME - 13.5 mo. PI | 116.5 ± 26.6 | 17.7 ± 1.6* |
|   |   | TME - 14.5 mo. PI | 105.4 ± 54.1 | 18.4 ± 2.4* |
|   |   | Non-Inoculated | 152.1 ± 55.5 | 14.9 ± 1.5 |

***$p < 0.001$,
**$p < 0.01$,
*$p < 0.05$; Mann-Whitney U test

EXAMPLE 3

Immunohistochemical Data

To evaluate the morphologic effects of TSE infection on the retina of cattle, retinas from cattle clinically affected with TME using standard histologic techniques and immunohistochemistry. Immunoreactivity for PrP$^{Sc}$ was detected in the retinas of all TME cattle, and was localized primarily to the synaptic layers and the cytoplasm of retinal ganglion cells (FIG. 4B). Despite marked PrP$^{Sc}$ accumulation within the retinas of TME-affected cattle, severe pathologic change was not observed on examination of hematoxylin and eosin stained sections (FIG. 4A and FIG. D). However, multifocal distinct, round vacuoles (consistent with spongiform change) were observed within the IPL of TME affected cattle, but not in controls (arrows FIG. 4D). Cell density within the GCL differed between the two groups with controls having an average of 114 nuclei per five 40× fields versus 44 nuclei per five 40× fields in TME-affected cattle. Additionally, the optic nerves of TME-affected cattle contained numerous spongiform lesions of 5 μm to 25 μm in diameter Immunohistochemistry Antibodies directed against retinal cell types contributing to the ERG b-wave (rod bipolar cells and Müller glia) were used to examine these cell populations in cattle clinically affected with TME. Markers of rod bipolar cells and Müller glia have been shown to be altered in sheep with scrapie. Markers of rod bipolar cells include the alpha isoform of protein kinase C (PKCα) and vesicular glutamate transporter 1 (VGLUT1). Compared to controls, VGLUT1-IR in retinas from TME-affected 6 cattle was less obviously associated with larger bipolar cell terminals along the vitreal border of the IPL (FIG. 5B and FIG. 5F).

In the retina, markers of Müller glia include glutamine synthetase (GS), and for reactive Müller glia, glial fibrillary acidic protein (GFAP) (Lewis G P, Fisher S K). Although subtle, higher levels of GS-IR were observed in the processes of Müller glia, specifically the portion coursing through the IPL, in TME-affected cattle versus controls (FIG. 5C and FIG. 5G). Immunoreactivity for GFAP was detected in the optic fiber layer of both control and TME-affected cattle, but markedly fewer and less prominent immunoreactive radial processes were observed in control retina compared to TME-affected retina (FIG. 5D and FIG. 5H).

The distribution of PrP$^{Sc}$ and various retinal cell type-specific markers in the retinas of 2 control and 5 TME-affected cattle were examined. Slides were immunolabeled to detect PrP$^{Sc}$ as previously described using primary antisera containing monoclonal antibodies F89/160.5 21 and F99/97.6.1 22 each at a concentration of 5 μM/ml. With each batch of slides labeled for PrP$^{Sc}$, serial sections of brainstem from a known positive sheep also were labeled for PrP$^{Sc}$ to assess any variability between batches and additional slides were processed with the omission of the primary antibody to control for nonspecific labeling. Sections immunolabeled to detect retinal cell type specific antigens were deparaffinized in xylene and rehydrated in a decremental alcohol series. Tissue sections were washed in 0.5 M potassium phosphate buffered solution (KPBS), and incubated for two hours in blocking solution containing 1% bovine serum albumin (BSA), 0.4% Triton X-100, and 1.5% normal donkey serum (NDS). Tissue sections were incubated in primary antibody (see below) overnight. On the following day, tissue sections were washed in KPBS containing 0.2% Triton X-100 and incubated for two hours in the appropriate fluorophore-conjugated secondary antibody. Sections were washed again, incubated in 4',6-diamidine-2-phenylindole (DAPI; Molecular Probes, Carlsbad, Calif.) for 5 minutes, and washed a final time in KPBS prior to being cover-slipped with Vectashield fluorescence mounting medium (Vector, Burlingame, Calif.). Labeling patterns were imaged with a fluorescence-capable microscope (Nikon Eclipse E800) equipped with a digital camera, and prepared using Adobe Photoshop CS Version 8.0 and Macromedia Freehand MX Version 11.0 for the Macintosh.

Primary antibodies used in this study included the following: rabbit anti-protein kinase C-alpha isoform (PKC) (Sigma, St. Louis, Mo.); guinea pig anti-vesicular 11 glutamate transporter 1 (VGLUT1) (Chemicon International, Inc., Temecula, Calif.); rabbit anti-microtubule-associated protein 2 (MAP2) (Chemicon International, Inc., Temecula, Calif.); rabbit anti-glutamine synthetase (GS) (Sigma, St. Louis, Mo.); and rabbit anti-glial fibrillary acidic protein (GFAP) (DakoCytomation, Carpinteria, Calif.). Secondary antibodies included fluorescein isothiocyanate (FITC)-conjugated donkey anti-guinea pig IgG (Jackson ImmunoResearch, West Grove, Pa.); or FITC-conjugated donkey anti-rabbit IgG (Jackson ImmunoResearch, West Grove, Pa.).

EXAMPLE 4

ERG of Scrapie Inoculated Suffolk Sheep

A single Suffolk sheep (number 3742) was inoculated intracerebrally with brain homogenate prepared from a fourth-passage scrapie-affected sheep. The original source of inoculum was from 13 scrapie-affected sheep from 7 flocks (designated 13-7). These sheep were verified scrapie positive by immunohistochemistry for $PrP^{Sc}$. The inoculum was ground in a mechanical grinder, gentamicin was added at 10 μg/ml, and the final concentration of 10% (wt/vol) was made with PBS. For subsequent passages the scrapie-infected brain tissue was obtained from the animal with the shortest incubation to terminal disease (survival) time from the previous passage and the inoculum was prepared as described (supra). The inoculum was passaged in 5 generations of lambs. Sheep #3742 was from the $5^{th}$ generation of lambs ($4^{th}$ passage) and had a 12.2-month survival time.

The procedure for intracerebral inoculation is similar to cattle. Briefly, the animals were sedated with xylazine, a midline incision was made in the skin at the junction of the parietal and frontal bones, and a 1-mm hole was drilled through the calvarium. The inoculum (1 ml of 10% wt/vol brain homogenate) was injected into the midbrain via a 22-gauge 9 cm long needle while withdrawing the needle from the brain. The skin incision was closed with a single suture. Inoculated animals were held in biosafety level 2 facilities for 2 weeks post-inoculation and then were transferred to outside pens. They were fed pelleted growth and maintenance rations that contained no ruminant proteins, hay, and water ad lib. At 10 and 12.5 months post-inoculation, electroretinographs were conducted under the conditions and with the equipment detailed supra at light intensity of 2.45 cd·s/m² for scotopic and photopic conditions (EPIC 4000, LKC Technologies). At 12.5 months, the sheep displayed clinical signs of TSE characterized by cachexia and ataxia. ERGs were collected at the 10 month post-inoculation. ERGs at the 12.5 date under scotopic conditions for the infected sheep was collected, however an ERG response under photopic conditions could not be elicited. The scrapie-affected sheep was euthanized thereafter.

Eight age-matched non-inoculated, scrapie-free, Suffolk sheep served as the ERG control group. The b-wave values were averaged for the control sheep group.

As detailed in Table 2, scotopic electroretinogram collected at the 12.5 month post-inoculation revealed a decrease in b-wave amplitude of approximately 54.3 percent with respect to the pre-clinical stage under scotopic conditions. Similarly, the 12.5 month post-inoculation sheep had an approximate 86.5 percent increase in b-wave implicit time with respect to the pre-clinical stage under scotopic conditions. In comparing the clinical stage sheep with the control group under scotopic conditions, the b-wave amplitude decreased approximately 39.8 percent with an approximate 85.8 percent increase of implicit time for the 12.5 month post-inoculated sheep.

TABLE 2

|  | Control | Sheep 3742 10 months post-inoculation | Sheep 3742 12.5 months post-inoculation |
| --- | --- | --- | --- |
| Scotopic b-wave amplitude (μV) | 405.2 +/− 153.8 | 534.7 | 244.1 |
| Scotopic b-wave implicit time (candela seconds per meter squared) | 26.1 +/− 7.1 | 26.0 | 48.5 |
| Photopic b-wave amplitude (μV) | 178.6 +/− 88.3 | 124.5 | No recordable ERG |
| Photopic b-wave implicit time (candela seconds per meter) | 12.4 +/− 2.5 | 8.0 | No recordable ERG |

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. A method for screening transmissible spongiform encephalopathy in livestock of the genus *Bos* via an electroretinogram, the method comprising:
arranging electroretinogram electrodes on the eye of the livestock,
producing and recording from said electrodes a biphasic electroretinogram waveform having an a-wave and b-wave from livestock retina in response to photic stimulus under scotopic conditions,
measuring the amplitude of the b-wave, wherein the amplitude is measured from the trough of the a-wave to the peak of the b-wave,
measuring the implicit time of the b-wave, wherein the implicit time is measured from onset of photic stimulus to b-wave peak,
comparing said recorded waveform to a comparative waveform of livestock of the genus *Bos* known not to have transmissible spongiform encephalopathy and;
determining whether the recorded waveform has a decreased b-wave amplitude of approximately 22 percent to approximately 24 percent less than the comparative waveform or an increased b-wave implicit time of approximately 23 percent to approximately 34 percent greater than the comparative waveform, wherein a decreased b-wave amplitude or increased b-wave implicit time is indicative of the screened *Bos* livestock as having transmissible spongiform encephalopathy.

2. The method of claim 1 wherein said livestock of the genus *Bos* to be screened does not exhibit any behavior of transmissible spongiform encephalopathy.

3. A method for screening transmissible spongiform encephalopathy in livestock of the genus *Bos* via an electroretinogram, the method comprising:
arranging electroretinogram electrodes on the eye of the livestock,
producing and recording from said electrodes a biphasic electroretinogram waveform having an a-wave and b-wave from livestock retina in response to photic stimulus under photopic conditions, measuring the amplitude of the b-wave, wherein the amplitude is measured from the trough of the a-wave to the peak of the b-wave, measuring the implicit time of the b-wave, wherein the implicit time is measured from onset of photic stimulus to b-wave peak; and comparing said recorded waveform to a comparative waveform of livestock of the genus *Bos* known not to have transmissible spongiform encephalopathy, determining whether the recorded waveform has a decreased b-wave amplitude of approximately 20 percent to approximately 31 percent less than the comparative waveform or an increased b-wave implicit time of approximately 18 percent to approximately 23 percent greater than the comparative waveform, wherein a decreased b-wave amplitude or increased b-wave implicit time is indicative of the screened *Bos* livestock as having transmissible spongiform encephalopathy.

4. The method of claim 3 wherein said livestock of the genus *Bos* to be screened does not exhibit any behavior of transmissible spongiform encephalopathy.

5. A method for screening transmissible spongiform encephalopathy in livestock of the genus *Ovis* via an electroretinogram, the method comprising:

arranging electroretinogram electrodes on the eye of the livestock, producing and recording from said electrodes a biphasic electroretinogram waveform having an a-wave and b-wave from livestock retina in response to photic stimulus under scotopic conditions, measuring the amplitude of the b-wave, wherein the amplitude is measured from the trough of the a-wave to the peak of the b-wave, measuring the implicit time of the b-wave, wherein the implicit time is measured from onset of photic stimulus to b-wave peak, comparing said recorded waveform to a comparative waveform of livestock of the genus *Ovis* known not to have transmissible spongiform encephalopathy, determining whether the recorded waveform has a decreased b-wave amplitude of approximately 39 percent to approximately 54 percent less than the comparative waveform or an increased b-wave implicit time of approximately 89 percent greater than the comparative waveform, wherein a decreased b-wave amplitude or increased b-wave implicit time is being indicative of the screened *Ovis* livestock as having transmissible spongiform encephalopathy.

6. The method of claim 5 wherein said livestock of the genus *Ovis* to be screened does not exhibit any behavior of transmissible spongiform encephalopathy.

* * * * *